US011083832B2

(12) United States Patent
Khair (10) Patent No.: US 11,083,832 B2
(45) Date of Patent: Aug. 10, 2021

(54) OPTICAL DETECTION OF AIR BUBBLES IN EITHER SALINE OR BLOOD OR A MIXTURE OF BOTH

(71) Applicant: Fresenius Medical Care Holdings, Inc., Waltham, MA (US)

(72) Inventor: Mohammad M. Khair, Irvine, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 16/749,940

(22) Filed: Jan. 22, 2020

(65) Prior Publication Data

US 2020/0155749 A1 May 21, 2020

Related U.S. Application Data

(63) Continuation of application No. 15/483,495, filed on Apr. 10, 2017, now Pat. No. 10,576,196.

(51) Int. Cl.
*A61M 1/36* (2006.01)
*G01N 33/49* (2006.01)

(52) U.S. Cl.
CPC ........... *A61M 1/3626* (2013.01); *G01N 33/49* (2013.01); *A61M 2205/3313* (2013.01)

(58) Field of Classification Search
None
See application file for complete search history.

(56) References Cited

U.S. PATENT DOCUMENTS

| 4,299,487 A | 11/1981 | Sengoku et al. |
| 5,589,935 A | 12/1996 | Biard |
| 5,800,361 A | 9/1998 | Rayburn |
| 6,862,534 B2 | 3/2005 | Sterling et al. |
| 7,661,293 B2 | 2/2010 | Dam |
| 7,661,294 B2 | 2/2010 | Dam |
| 7,671,974 B2 | 3/2010 | O'Mahony et al. |
| 8,091,407 B2 | 1/2012 | Schneider et al. |
| 8,104,348 B2 | 1/2012 | Balschat et al. |

(Continued)

FOREIGN PATENT DOCUMENTS

| CN | 1059404 A | 3/1992 |
| CN | 1153463 A | 7/1997 |

(Continued)

OTHER PUBLICATIONS

"Teaching Medical Physics: Pulse Oximeters," https://www.iop.org/education/teacher/resources/teaching-medical-physics/pulse/file_56276.pdf, Institute of Physics (2012).

(Continued)

*Primary Examiner* — Richard C Gurtowski (74) *Attorney, Agent, or Firm* — Leydig, Voit & Mayer, Ltd.

(57) ABSTRACT

Embodiments of the disclosure provide a system and method for detection of a transient air bubble in an arterial blood flow path during dialysis (e.g., hemodialysis). The system uses measurements from an optical sensor to remove one or more effects of common factors affecting the absorbance of the light incident on the arterial tubing. These factors include color of medium within the arterial tubing, tubing color, angle of illumination, and temperature of the optical detector. A variance of the measurements from the optical sensor are used to determine whether an air bubble is present.

22 Claims, 5 Drawing Sheets

(56) References Cited

U.S. PATENT DOCUMENTS

| | | |
|---|---|---|
| 8,130,369 B2 | 3/2012 | Barrett et al. |
| 8,631,683 B2 | 1/2014 | Dam et al. |
| 9,173,988 B2 | 11/2015 | Barrett et al. |
| 9,194,792 B2 | 11/2015 | Barrett et al. |
| 9,250,216 B2 | 2/2016 | Wright et al. |
| 9,265,872 B2 | 2/2016 | Zhang |
| 9,272,089 B2 | 3/2016 | Jacobson et al. |
| 2004/0019431 A1 | 1/2004 | Sterling et al. |
| 2008/0184784 A1 | 8/2008 | Dam |
| 2012/0095306 A1 | 4/2012 | Egozi |
| 2012/0120384 A1 | 5/2012 | Barrett et al. |
| 2015/0346092 A1 | 12/2015 | Lee et al. |

FOREIGN PATENT DOCUMENTS

| | | |
|---|---|---|
| CN | 101269246 A | 9/2008 |
| CN | 102065765 A | 5/2011 |
| CN | 102872488 A | 1/2013 |
| CN | 103796709 A | 5/2014 |
| CN | 205729374 U | 11/2016 |
| CN | 106178157 A | 12/2016 |
| EP | 0 401 453 A1 | 12/1990 |
| WO | WO 2004/019776 A1 | 3/2004 |
| WO | WO 2012/022456 A1 | 2/2012 |
| WO | WO 2013/155115 A1 | 10/2013 |

OTHER PUBLICATIONS

Toffaletti et al., "Effect of Small Air Bubbles on Changes in Blood pO2 and Blood gas Parameters; Calculated vs. Measured Effects," AcuteCareTesting.org, https://acutecaretesting.org/-/media/acutecaretesting/files/pdf/effect-of-small-air-bubbles-on-changes-in-blood-po2-and-blood-gas-parameterscalculated-vs-measured-effects.pdf (Jul. 2012).

International Patent Application No. PCT/US2018/025666, International Search Report (dated Jun. 15, 2018).

U.S. Appl. No. 15/483,495, filed Apr. 10, 2017.

Chinese Patent Application No. 201880024353.1, Search Report (dated Sep. 25, 2020).

European Patent Application No. 18 785 187.8, Search Report (dated Dec. 1, 2020).

OPTICAL DETECTION OF AIR BUBBLES IN EITHER SALINE OR BLOOD OR A MIXTURE OF BOTH

CROSS-REFERENCE TO RELATED APPLICATIONS

This patent application is a continuation of U.S. patent application Ser. No. 15/483,495, filed Apr. 10, 2017. which is incorporated by reference in its entirety.

BACKGROUND

Patients with kidney failure or partial kidney failure typically undergo hemodialysis treatment, often at a hemodialysis treatment center or clinic. When healthy, kidneys maintain the body's internal equilibrium of water and minerals (e.g., sodium, potassium, chloride, calcium, phosphorous, magnesium, and sulfate). The kidneys also function as part of the endocrine system to produce the hormone erythropoietin as well as other hormones. Hemodialysis is an imperfect treatment to replace kidney function, in part, because it does not correct the endocrine functions of the kidney.

In hemodialysis, blood is taken from a patient through an intake needle (or catheter) which draws blood from an artery located in a specific accepted access location (arm, thigh, subclavian, etc.). The drawn blood is pumped through extracorporeal tubing via a peristaltic pump, and then through a dialyzer which removes unwanted toxins such as blood urea, nitrogen, potassium, and excess water from the blood. As the blood passes through the dialyzer, it travels in straw-like tubes which serve as semi-permeable membrane passageways for the uncleaned blood. Fresh dialysate liquid, which is a solution of chemicals and water, flows through the dialyzer in the direction opposite the blood flow. As the dialysate flows through the dialyzer, it surrounds the straw-like membranes in the dialyzer. The fresh dialysate collects excess impurities passing through the straw-like tubes by diffusion, and also collects excess water through an ultrafiltration process due to a pressure drop across the membranes. The used dialysate exits the dialyzer with the excess fluids and toxins via an output tube, thus cleansing the blood flowing through the dialyzer. The dialyzed blood then flows out of the dialyzer via tubing and a needle (or catheter) back into the patient. Sometimes, a heparin drip or pump is provided along the extracorporeal blood flow loop in order to prevent clotting during the hemodialysis process. Several liters of excess fluid can be removed during a typical multi-hour treatment session. In the U.S., a chronic patient will normally undergo hemodialysis treatment in a dialysis center three times per week, either on Monday-Wednesday-Friday schedule or a Tuesday-Thursday-Saturday schedule.

Hemodialysis has an acute impact on the fluid balance of the body due in part to the rapid change in circulating blood volume. When the fluid removal rate is more rapid than the plasma refilling rate of the body, intravascular blood volume decreases. The resulting imbalance has been linked to complications such as hypotension, loss of consciousness, headaches, vomiting, dizziness and cramps experienced by the patient, both during and after dialysis treatments. Continuous quantitative measurement of parameters relating to the circulating blood volume (in real-time) during hemodialysis reduces the chance of dialysis-induced hypotension, and otherwise optimizes dialysis therapy regimes by controlling fluid balance and aiding in achieving the appropriate dry weight for the patient.

SUMMARY

One embodiment of the disclosure provides a method for detecting air bubbles in a blood flow path using at least one light emitter to generate different wavelengths and at least one photosensor. The method includes: setting initial intensities of light at each wavelength emanating from the at least one light emitter; determining intensities of light received at the at least one photosensor, wherein the light received at the at least one photosensor traverses the blood flow path; determining one or more normalized ratios using the initial intensities of light at each wavelength emanating from the at least one light emitter and the intensities of light at each wavelength received at the at least one photosensor; and determining whether an air bubble is present in the blood flow path based on the determined one or more normalized ratios.

Another embodiment of the disclosure provides a system for detecting air bubbles in a blood flow path. The system includes: at least one light emitter configured to generate different wavelengths; at least one photosensor; and a processor, configured to: set initial intensities of light at each wavelength emanating from the at least one light emitter; determine intensities of light received at the at least one photosensor, wherein the light received at the photosensor traverses the blood flow path; determine one or more normalized ratios using the initial intensities of light at each wavelength emanating from the at least one light emitter and the intensities of light at each wavelength received at the at least one photosensor; and determine whether an air bubble is present in the blood flow path based on the determined one or more normalized ratios.

Yet another embodiment of the disclosure provides a non-transitory computer-readable medium having processor-executable instructions for detecting air bubbles in a blood flow path using at least one light emitter to generate different wavelengths and at least one photosensor. The processor-executable instructions, when executed, facilitating performance of the following: setting initial intensities of light at each wavelength emanating from the at least one light emitter; determining intensities of light received at the at least one photosensor, wherein the light received at the at least one photosensor traverses the blood flow path; determining one or more normalized ratios using the initial intensities of light at each wavelength emanating from the at least one light emitter and the intensities of light at each wavelength received at the at least one photosensor; and determining whether an air bubble is present in the blood flow path based on the determined one or more normalized ratios.

DETAILED DESCRIPTION

In a renal dialysis treatment session, occlusion of an arterial blood access line due to blood flow at high flow rates (300-500 ml/min) may result in very low negative pressures (<200 mmHg) which would result in degassing of the blood. As such, air bubble detection is important for indicating whether an arterial occlusion has occurred. One way of optically detecting air bubbles is with a single light intensity wavelength. The optical air bubble detection on the arterial line can thus be used for indicating an arterial occlusion event and alarming a user. While optical air bubble detection is desirable, and can be achieved with a single light intensity wavelength, it is affected by several factors affecting the single light wavelength absorbance.

Single light wavelength absorbance is affected by the color of the medium or blood, which varies significantly based on the blood hematocrit concentration and oxygenation level. Single light wavelength is also affected by sensor to sensor variability across multiple sensors. A sensor includes a single wavelength source or emitter and a single wavelength detector. Sensor to sensor variability may be reduced through a self-normalization step where sensor measurements are normalized relative to a baseline of its measurement. For example, an empty tubing may be used with a sensor to characterize the sensor's profile while adjusting light input to the sensor. This self-normalization or sensor calibration can be performed on each source-detector combination to ensure signal integrity and sensor response at wavelength of interest.

Also during dialysis, the disposable tubing that contains blood and through which the optical detection is taking place undergoes discoloration and loses some of its transparency over time, thus affecting measurements relying on single light wavelength absorbance. Other factors affecting single light wavelength absorbance include transient effects during dialysis. For example, when a saline solution dose is introduced and mixes with blood, the blood becomes diluted the color of the medium contained in the tubing lightens. Furthermore, when the saline delivery ends, and blood returns to the tubing mixing with saline currently in the tubing, the color of the medium contained in the tubing darkens.

Saline delivery is typically clinically introduced during dialysis treatment in order to deliver medications to the patient, or in the case of a patient suffering from hypovolemia, saline is introduced to allow for rapid patient recovery. Such variability in factors affecting the absolute intensity of light absorption makes the detection of air based purely on intensity level of light of a single wavelength challenging and difficult to adapt with the various factors. Using a single wavelength, an optical sensor typically interprets detection of blood when the single wavelength light is mostly absorbed (or equivalently reduced transmission of light), thus resulting in a low-range sensor output. Using a single wavelength, the presence of air in the tubing produces scattering, which also reduces transmission, but not as much as blood, and thus resulting in a mid-range sensor output. Using a single wavelength, the presence of clear water or saline in the tubing results in focused transmission with little absorbance of the single wavelength light, thus resulting in a high-range sensor output. A single wavelength optical sensor may then be used to obtain "typical" levels of sensor outputs for blood, air, and saline in order to interpret contents of the tubing during dialysis.

Embodiments of the disclosure provide an improved methodology for detection of a transient air bubble by removing one or more effects of common mode factors affecting the absorbance of the light, such as, medium color, tubing color, angle of illumination, or temperature of the optical detector. In one embodiment, the methodology involves using a normalized ratio (R) of the absorbance intensity of two light wavelengths through the medium. By using the normalized ratio R, common factors affecting the absolute scale of light intensity are eliminated. Only factors affecting the wavelengths differently result in a change to the value and sensitivity of the normalized ratio R. When taking a ratio, their effects cancel out.

Figure 1:
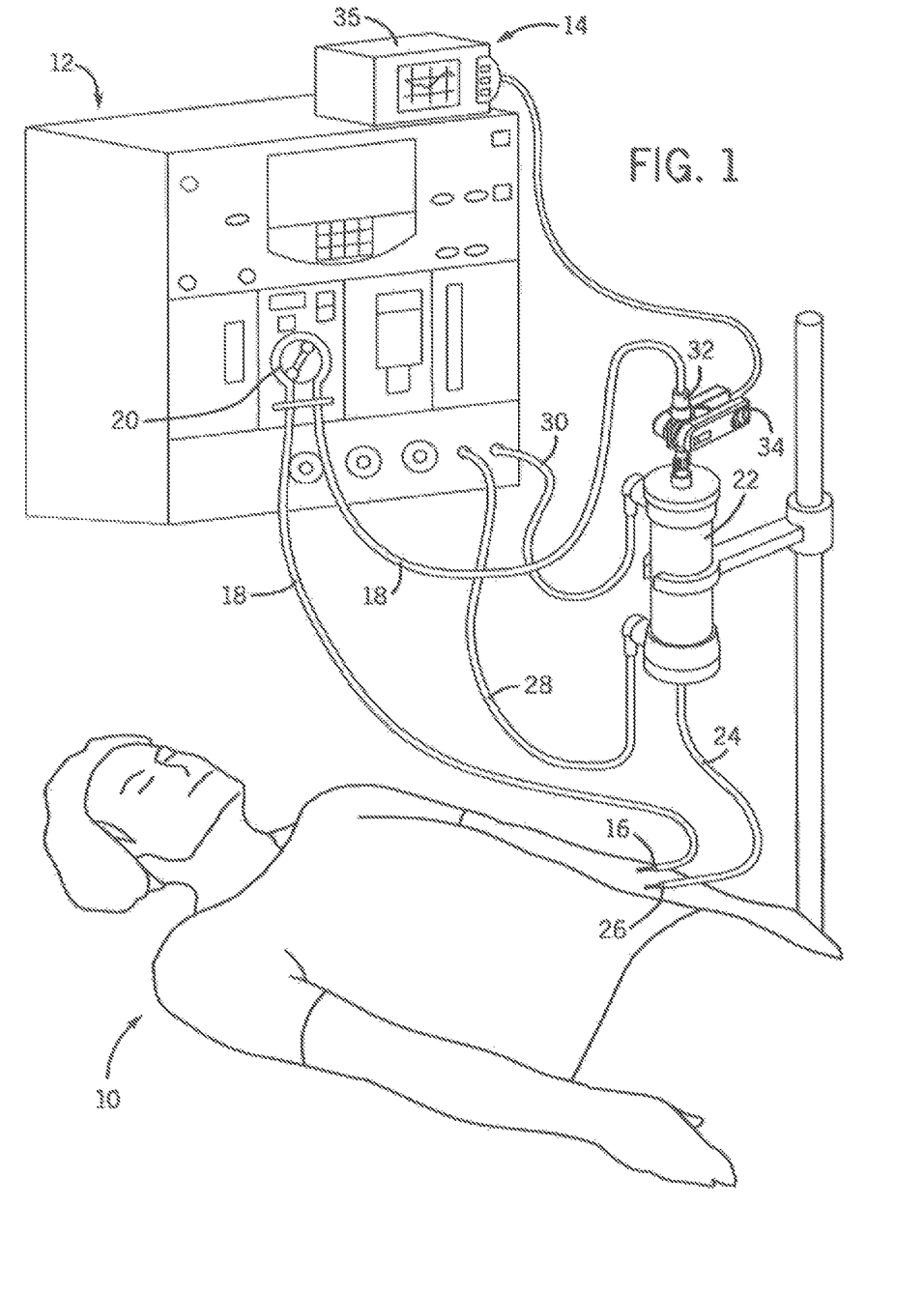
FIG. 1 is a perspective view of a typical patient undergoing hemodialysis treatment with a non-invasive, optical blood monitor monitoring the patient's blood in real-time as it passes through extracorporeal tubing in the hemodialysis system.

FIG. 1 is a perspective view of a typical patient undergoing hemodialysis treatment with a non-invasive, optical blood monitor monitoring the patient's blood in real-time as it passes through extracorporeal tubing in the hemodialysis system. The environment illustrated in FIG. 1 is usable with exemplary embodiments of the present disclosure. Further, it will be appreciated that the environment shown in FIG. 1 is merely exemplary, and that the principles discussed herein with respect to exemplary embodiments of the present disclosure may be implemented in other environments as well.

FIG. 1 illustrates a patient 10 undergoing hemodialysis treatment using a conventional hemodialysis system 12, as well as a non-invasive, optical blood monitor 14. A typical hemodialysis clinic will have several hemodialysis systems 12 for treating patients on a Monday-Wednesday-Friday schedule or a Tuesday-Thursday-Saturday schedule. While the invention is not limited to the number of hemodialysis systems located at a clinic, or the specific type of hemodialysis system, the general operation of the hemodialysis system 12 is helpful for understanding the environment in which the invention is intended to operate.

An input needle or catheter 16 is inserted into an access site of the patient 10, such as in the arm, and is connected to extracorporeal tubing 18 that leads to a peristaltic pump 20 and then to a dialyzer or blood filter 22. The dialyzer 22 removes toxins and excess fluid from the patient's blood. The dialyzed blood is returned from the dialyzer 22 through extracorporeal tubing 24 and return needle or catheter 26. In some parts of the world, the extracorporeal blood flow may additionally receive a heparin drip to prevent clotting. The excess fluids and toxins are removed by clean dialysate liquid which is supplied to the dialyzer 22 via tube 28 and removed for disposal via tube 30. A typical hemodialysis treatment session takes about 3 to 5 hours in the United States.

In the exemplary environment depicted in FIG. 1, the optical blood monitor 14 includes a blood chamber 32, an optical blood sensor assembly 34, and a controller 35. The blood chamber 32 is preferably located in line with the extracorporeal tubing 18 upstream of the dialyzer 22. Blood from the peristaltic pump 20 flows through the tubing 18 into the blood chamber 32. The preferred sensor assembly 34 includes LED photo emitters that emit light at optical wavelengths. The blood chamber 32 includes lenses so that the emitters and detectors of the sensor assembly 34 can view the blood flowing through the blood chamber 32, and determine whether a transient air bubble is detected in the blood.

In another exemplary environment, the optical blood monitor includes an optical blood sensor assembly and a controller and does not include a blood chamber. The optical blood sensor assembly clasps onto the extracorporeal tubing upstream of the dialyzer. The blood sensor assembly includes LED photo emitters that emit light in optical wavelengths including red light, infrared light, ultraviolet light, blue light, green light, and/or any wavelength in the optical spectrum. The emitted light travels from the LED photo emitters through the extracorporeal tubing to light detectors (e.g. photodiodes) also included in the optical blood sensor assembly.

Figure 2:
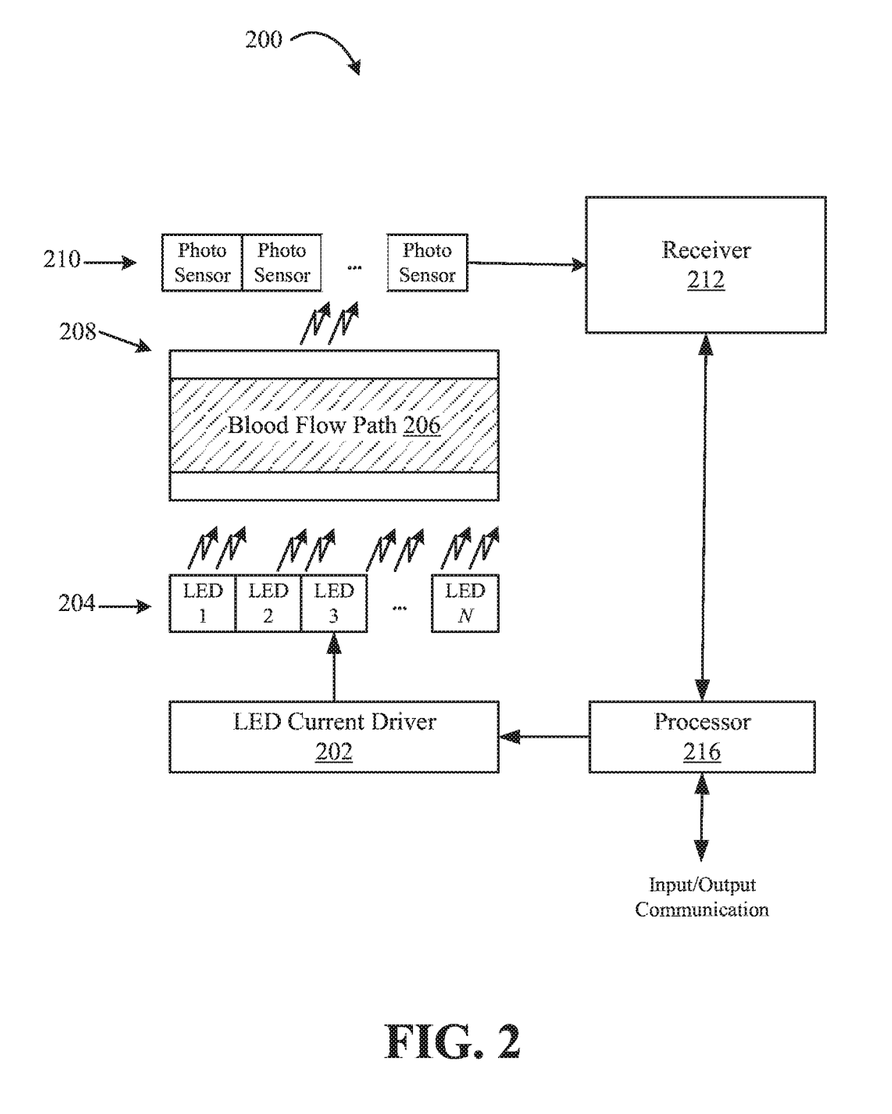
FIG. 2 illustrates an exemplary system for measuring blood constituents according to some embodiments of the disclosure.

FIG. 2 illustrates an exemplary system 200 that may be used to measure blood constituents using an optical blood sensor assembly according to some embodiments of the disclosure. An LED current driver 202 produces multiple currents to drive an LED array 204. The LED array 204 contains LED1 to LEDN. Each LED in the LED array 204 operates at a different wavelength, and the LED current driver 202 is configured to provide power to turn ON or turn OFF each LED in the LED array 204.

FIG. 2 shows that processor 216 controls the LED current driver 202, so in some embodiments, the processor 216 may determine which LEDs should be turned ON at a certain time during measurement. Light from the LED array 204 is incident on a blood container 208, passes through a blood flow path 206, and is detected at a photosensor 210 (or "photodetector") which may be a photodiode. The blood container 208 may be, for example, a blood chamber 32 located in line with an extracorporeal tubing 18, or may be, for example, the extracorporeal tubing 18 itself. The photosensor 210 may be one or more photosensors sensitive to wavelengths emitted by the LED array 204. The photosensor 210 collects and integrates detected LED light and generates a current. The current is then amplified and filtered by the receiver 212. The receiver 212 may also convert the amplified and filtered current from an analog signal to a digital signal, providing the digital signal to the processor 216 for further analysis.

The processor 216 is designed to interface with other electronic components allowing input and output communication of signals to and from the optical blood sensor assembly. For example, apart from the blood container 208 including the blood path 206, every other component identified in system 200 may be part of a optical blood sensor assembly, for example, an optical blood sensor assembly 34 as depicted in FIG. 1. Using the embodiment in FIG. 1, the optical blood sensor assembly 34 may communicate with a controller 35 for displaying system outputs and/or receiving command signals or calibration signals.

In some embodiments, the processor 216 performs calculations and analyses based on the digital signal received from the receiver 212 and determines whether air bubbles are present in the blood flow path 206. In other embodiments, the processor 216 may provide the digital signal received from the receiver 212 to an external computing device using the input/output communication channels so that the external computing device, for example, controller 35, determines whether air bubbles are present in the blood flow path 206. Processor 216 may be a microprocessor, a microcontroller, a field programmable gate array (FPGA), a complex programmable logic device (CPLD), an application specific integrated circuit (ASIC), etc.

Figure 2A:
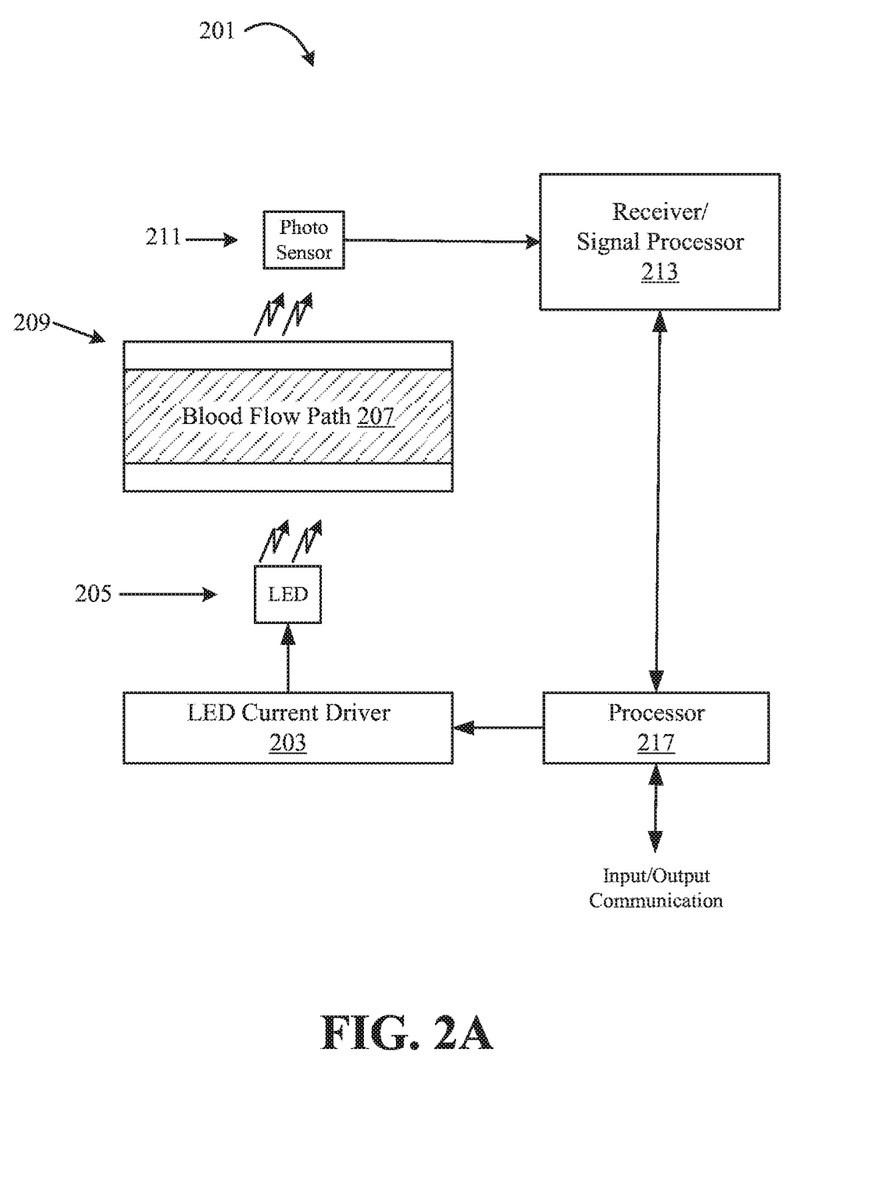
FIG. 2A illustrates another exemplary system for measuring blood constituents according to some embodiments of the disclosure.

FIG. 2A illustrates another exemplary system 201 that may be used to measure blood constituents using an optical blood sensor assembly according to some embodiments of the disclosure. The system 201 includes a processor 217, LED current driver 203, a multi-wavelength LED 205, a blood flow path 207, a tubing 209, a wideband photosensor 211, and a receiver/signal processor 213. The multi-wavelength LED 205 may generate more than one wavelength, and the wideband photosensor 211 is sensitive to the more than one wavelength generated by the multi-wavelength LED 205. The receiver/signal processor 213 is configured to obtain a current from the photosensor 211 and separate the magnitude of the current contributions of the different wavelengths sensed by the wideband photosensor 211. The receiver/signal processor 213 may separate the current contributions from the different wavelengths using digital and/or analog signal processing. The receiver/signal processor 213 then provides the separated current contributions to the processor 217.

The exemplary systems depicted in FIG. 2 and FIG. 2A may be used for detection of air bubbles by continuous monitoring of a blood flow path. The Beer-Lambert law defines the concentration $c_i$ of an absorbent in solution to be determined by the intensity of light transmitted through the solution, knowing the path length $d_\lambda$, the intensity of the incident light $I_{0,\lambda}$, and the extinction coefficient $\varepsilon_{i,\lambda}$, at a particular wavelength $\lambda$. In generalized from, the Beer-Lambert law is expressed as Eq. (1):

$$I_\lambda = I_{0,\lambda} \times e^{d_\lambda \times \mu_{a,\lambda}} \qquad (Eq.\ 1)$$

where $\mu_{a,\lambda} = \Sigma_{i=1}^{n} \varepsilon_{i,\lambda} \times c_i$, and where a is the bulk absorption coefficient that represents the probability of absorption per unit length, assuming photon scattering in the solution is negligible.

In an exemplary embodiment, the detected absorbance of a first light wavelength's intensity, called $I_A$, is divided by the detected absorbance of a second light wavelength's intensity, called $I_B$, thus producing a ratio of $R=I_A/I_B$, which represents the normalized ratio R of Beer-Lambert's light intensity at wavelength A over the Beer-Lambert light intensity at wavelength B. Note that $I_A$ and $I_B$ represent detected absorbance parameters. Detected absorbance is defined as light intensity absorbed by absorbents in the medium or solution as defined in the Beer-Lambert law. The detected absorbance may be obtained through a source-detector measurement system by subtracting the light intensity received at the detector from the light intensity provided at the source. For example, in FIG. 2, LED1 in LED array 204 emits 810 nm wavelength light with intensity $I_{emit,810\ nm}$, and the light travels through the blood flow path 206 and is incident on one photosensor in photosensor 210. The processor 216 determines the light intensity to be $I_{detect,810\ nm}$. The detected absorbance $I_{810\ nm}$ is determined as $I_{emit,810\ nm} - I_{detect,810}$ nm.

The ratio $R=I_A/I_B$ normalizes all common components affecting the plurality of light wavelengths' absorbance intensity. The ratio R will therefore be limited in its sensitivity to the actual factors distinctly affecting the light wavelengths individually as opposed to common factors affecting all wavelengths' intensities. Such normalization methods are effective in limiting the sensitivity of the detection ratios to the transient factors, such as, air bubble presence.

During dialysis, the color of the medium in the tubing, for example, the extracorporeal tubing 18, presents itself as a persistent value to the absorbance variable that is slowly varying. For example, the color of the medium when changing from blood to saline and back to blood will take on a gradual, slowly changing transient characteristic with an intermediary that is a mixture of both saline and blood. When air bubbles are present, however, a rapid variation occurs in the measured absorbance of the medium. Therefore, in some embodiments, a variance of the measured absorbance in the blood flow path 206 may be used to detect the presence of air bubbles. Embodiments of the disclosure thus provide an ability to avoid false alarms due to gradual changes in color of the medium (blood or saline or mixture thereof) caused by slow-varying transitions in the respective concentrations of blood and saline. Blood tubing color changes are also eliminated since these color changes are also slowly varying compared to air bubble presence. As such, the system is more robust and reliable for air bubble detection for arterial occlusion indication.

Due to the transient nature of the composition of the medium, a sampling rate may be defined for the measurement system of FIGS. 1, 2 and 2A. For example, the optical sensor assembly 34 may make measurements with a sampling rate varying from 100 Hz to 1000 Hz. The sampling rate should be fast enough to realize fast passing transient bubble events under flowing fluid conditions.

In an exemplary embodiment, the optical sensor assembly 34 includes an LED that emits light in a red light wavelength, an LED that emits light in an infrared wavelength, a photosensor sensitive to red light wavelengths, and a photosensor sensitive to infrared wavelengths. Since the photosensors are sensitive to specific wavelength regimes, the LED-photosensor pairs for the red light wavelength and the infrared wavelength are operated at the same time to obtain measurements. That is, both LEDs are ON at the same time, and both photosensors are receptive at the same time to obtain simultaneous measurements at the red light wavelength and the infrared wavelength. A normalized ratio can then be determined based on the measurements.

Figure 3:
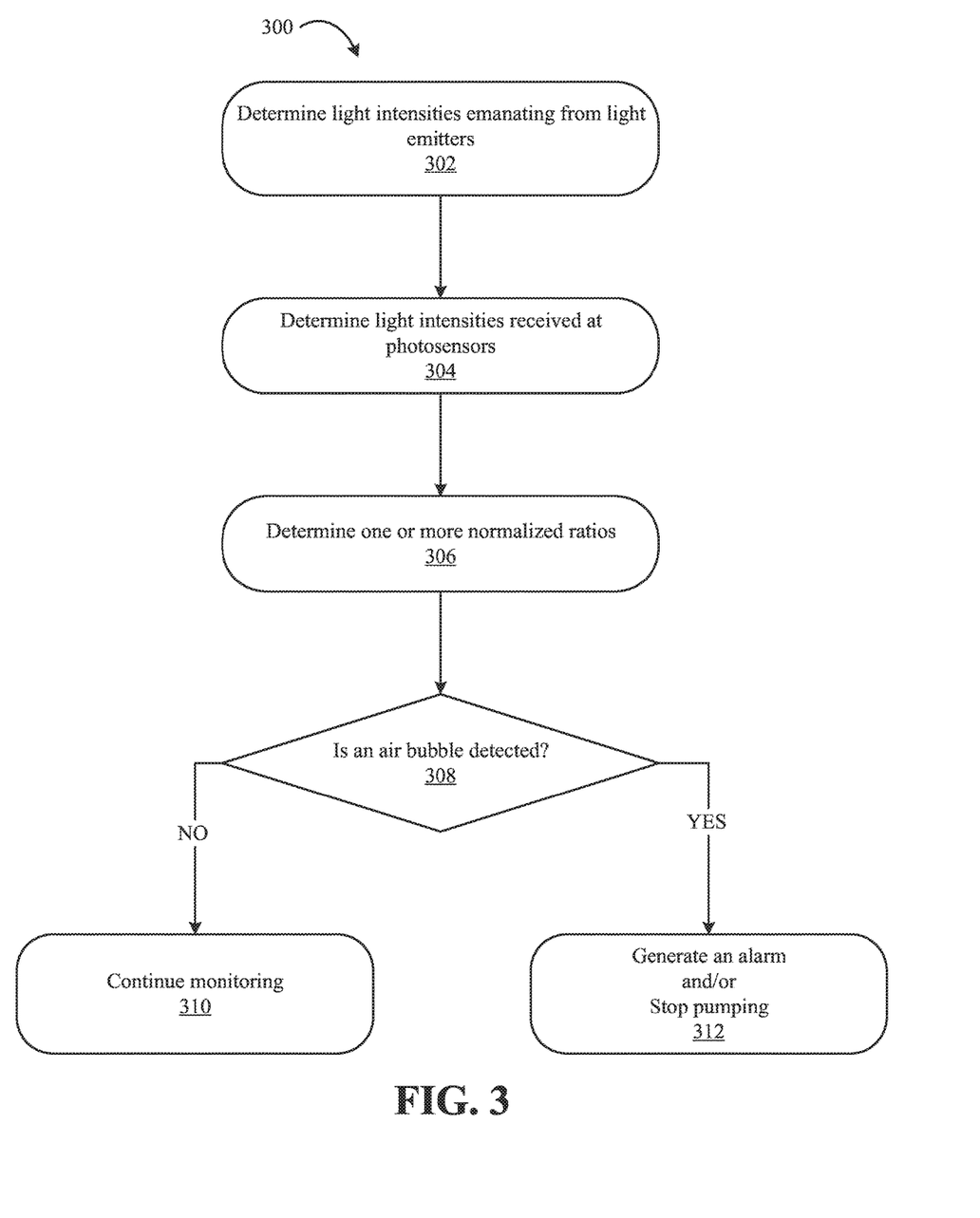
FIG. 3 illustrates a process of detecting an air bubble according to some embodiments of the disclosure.

FIG. 3 illustrates an exemplary process 300 of detecting an air bubble according to some embodiments of the disclosure. The process 300 may be performed, for example, using the optical sensor assembly 34 in the environment illustrated in FIG. 1. In the setup of FIG. 1, light sources in the optical sensor assembly 34 are turned ON. At step 302, the light intensities emanating from light emitters are determined. Using the illustration in FIG. 2, light emitters or light sources are the LED array 204. Light intensity of an LED in the LED array 204 is directly proportional to electrical current flowing through the LED. The processor 216 controls the LED current driver 202, which provides electrical current to the LED array 204, thereby controlling the light intensity of LEDs in the LED array 204. As such, at step 302, the processor 216 knows the current provided to an LED by the LED current driver 202 (which corresponds to the output intensity for the LED). For example, if two LEDs are in the LED array 204, with a first LED operating in the red light wavelength and the second LED operating in the infrared wavelength, the processor 216 determines the current provided to the first LED ($i_{emit,A}$) and the current provided to the second LED ($i_{emit,B}$).

At step 304, the light intensities detected at the photosensors are determined. A photosensor may generate a current proportional to an intensity of light incident upon the photosensor. For example, in accordance with FIG. 2, two photosensors are provided: a first photosensor (sensitive to light in the red light wavelength) and a second photosensor (sensitive to light in the infrared wavelength). After the light emanating from each of the first LED and the second LED travels through the blood flow path 206, the intensity of the light in each wavelength is changed. The light received at the first photosensor and the second photosensor causes a current proportional to the light intensity to be generated at each respective photosensor. Note that the first photosensor is sensitive to red light wavelength and will generate current proportional to only red light wavelength received, and the second photosensor is sensitive to infrared wavelength and will generate current proportional to infrared wavelength received. The receiver 212 then processes each current generated by each photosensor. The receiver 212 may have multiple channels to receive multiple currents from multiple photosensors detecting light at different wavelengths. The processor 216 receives from the receiver 212 a value for the current detected at the first photosensor ($i_{detect,A}$) and a value for the current detected at the second photosensor ($i_{detect,B}$).

At step 306, one or more normalized ratios are determined from light intensities absorbed in the blood flow path 206. That is, the normalized ratios are determined using the emanating light intensities obtained at step 302 and the received light intensities measured at step 304. For example, in accordance with FIG. 2, the processor 216 determines a normalized ratio R using $i_{emit,A}$, $i_{emit,B}$, $i_{detect,A}$, and $i_{detect,B}$. Determining the normalized ratio R involves first subtracting $i_{detect,A}$ from $i_{emit,A}$ and subtracting $i_{detect,B}$ from $i_{emit,B}$ to obtain current differences $i_A$ and $i_B$, respectively. The current differences $i_A$ and $i_B$ are proportional the light intensities of red light wavelength and infrared wavelength, respectively, that are absorbed in the blood flow path 206. The normalized ratio R then equals $i_A/i_B$.

At step 308, the processor 216 or a measurement system, for example, controller 35 determines whether an air bubble is detected. Step 308 involves comparing historical values of the normalized ratio R to determine a change in the normalized ratio R. For example, steps 302, 304, and 306 were performed at a previous time, and a normalized ratio $R_{prev}$ was stored in a non-transitory computer readable medium accessible by the measurement system. The measurement system then determines the change in the normalized ratios R and $R_{prev}$, normalized ratios at the current time period and the previous time period, respectively. If the change from a previous time period to a next time period meets or exceeds a predetermined threshold, the measurement system determines that an air bubble is detected. The system may then take an appropriate action at step 312 in response to detecting an air bubble, such as generating an alarm or stopping the pumping operation. The alarm may include, for example, an auditory alert generated at the controller 35, a visual alert such as a message or graphic displayed at the controller 35 or some other measurement system, or other forms of auditory, visual, data logging, and/or haptic notifications. Additionally or alternatively, the measurement system may automatically stop a pump, for example, the peristaltic pump 20 associated with pumping blood from the patient 10 through the dialyzer 22.

If the change from the previous time period to the next time period is below the predetermined threshold, the measurement system continues monitoring the normalized ratios at step 310 by performing steps 302, 304, and 306 to obtain a new normalized ratio for comparison at step 308.

The detection of an air bubble at step 308 may indicate a degassing of blood—i.e., that the blood is under extreme negative pressure. Negative pressure signifies that there is an occlusion or collapse in the blood flow path, and continuing to pump under these conditions generates more negative pressure and may cause further complications. Thus, it is advantageous in certain situations to stop the pump when an air bubble is detected.

For example, if an arterial wall collapse causes an air bubble, stopping the pump gives a caregiver time for the artery walls to expand before resuming operation at a slower flowrate. In some cases, the caregiver may gradually increase or ramp up the flowrate from the slower flowrate to a higher flowrate. Different patients come with different artery compliances, and attempting to pull blood from a collapsed artery will not result in blood being pulled. Thus, embodiments of the disclosure provide a system that detects when an artery wall collapses and alerts caregivers so they may reduce the flowrate of the peristaltic pump 20 to match a patient's artery compliance.

In another example, if a needle being lodged against the arterial wall causes an air bubble, stopping the pump gives a caregiver the chance to adjust the needle and restart the pulling of blood from the patient. The needle being lodged against the arterial wall blocks the blood flow path, thus creating negative pressure that may result in the creation of air bubbles.

In yet another example, if a kink in tubing causes an air bubble, stopping the pump gives a caregiver the chance to adjust the tubing and restart the pulling of blood from the patient.

Process 300 involves monitoring the rate of change of the normalized ratio R over time. This may be accomplished using a predefined sampling rate, for example, a sampling rate between 100 Hz and 1000 Hz. Thus, a normalized ratio R is determined at specific times, and the receiver 212 can sample the current generated at the photosensors at the specified sampling rate. In this configuration, there is no need to turn the LED array 204 ON and OFF during measurements.

In another embodiment, more than two wavelengths may be used. For example, if a third wavelength is introduced, then the system may obtain further ratios across the three wavelengths, including, $R_1=I_A/I_B$, $R_2=I_A/I_C$, $R_3=I_B/I_C$. When more than two ratios are used, medium absorbance (e.g., absorbance of blood) will be a function of the multiple ratios. For example, in an embodiment with three ratios $R_1$, $R_2$, and $R_3$, the medium absorbance may be written as $f(R_1, R_2, R_3)$. Linear regression methods may be used to define the characteristic of the function f.

In the case where three wavelengths are used, absorbances $I_A$, $I_B$, $I_C$ can provide three ratios $I_A/I_B$, $I_A/I_C$ or $I_B/I_C$. The process for detecting an air bubble using three wavelengths is similar to that for two wavelengths, except that more permutations of comparisons are possible. Potential advantages to having more than two wavelengths include: (1) different ratio results may reveal additional information, or (2) one ratio's results may be used to confirm another ratio's results. Also, using more than two wavelengths and obtaining more than one ratio provides the ability to adjudicate confusing or mixed results. For example, in the case where three wavelengths are used, if historical values of $R_1$ show an air bubble is present while historical values of $R_2$ and $R_3$ show that no air bubble is present, then the measurement system may not generate an alarm since two ratios out of three indicate no air bubble. Thus, the use of more than two wavelengths may yield more robust true positives.

Figure 4:
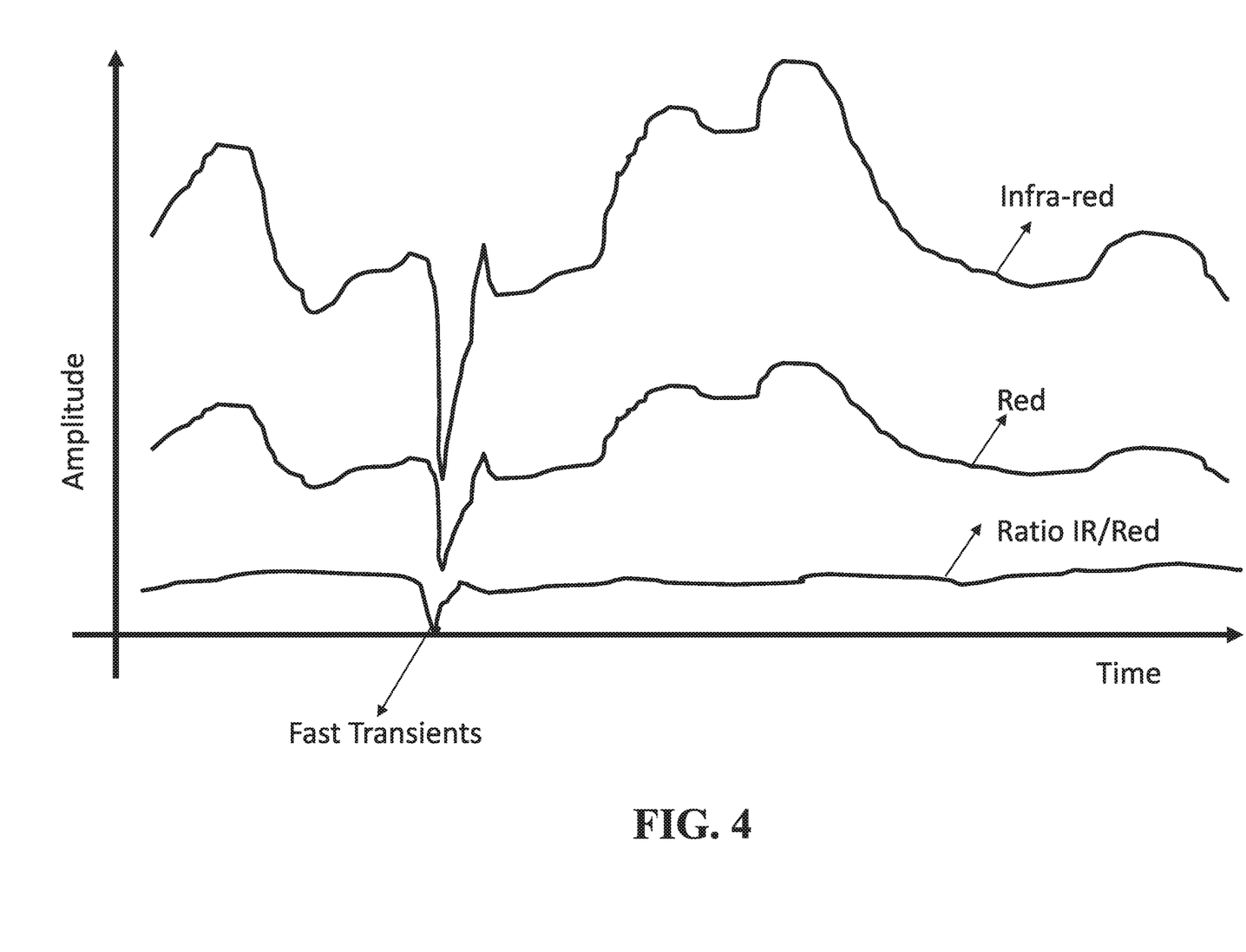
FIG. 4 illustrates example waveforms showing absorbance characteristics and a ratio of the absorbances.

FIG. 4 illustrates example waveforms showing absorbance characteristics and a ratio of the absorbances. Absorbance detected by an infrared sensor is shown compared to absorbance detected by a red wavelength sensor, and the ratio of the absorbances is obtained by dividing the absorbance detected by the infrared sensor by that detected by the red wavelength sensor. The absorbance characteristics plotted in FIG. 4 are sample measurements that may be obtained while monitoring a tubing with different transients due to a change in the medium contained in the tubing. As shown in FIG. 4, as the medium changes, the absorbance characteristics change accordingly, thus the red wavelength sensor and the infrared sensor have a similar shape with different amplitudes. The differing amplitudes suggest that one wavelength is absorbed more by the medium and tubing properties than the other wavelength.

The effect of common mode is removed when looking at the ratio of the absorbances. The ratio of the absorbances is mostly flat and non-varying compared to each absorbance characteristic used to determine the ratio. Effects of the color of the medium within the tubing or slowly varying color of the tubing are effectively removed when looking at the ratio. Thus, the ratio does not vary as much when compared to each of the absorbance characteristics.

The rate of change of the ratio can be used to detect fast transients as shown in FIG. 4. Fast transients are indicative of the presence of an air bubble. By taking the ratio of absorbances, slowly varying effects are muted, but fast transients will be captured and will be easily distinguished. Thus, as can be seen in FIG. 4, the fast transients corresponding to the present of an air bubble can clearly be seen when looking at the ratio of the absorbances over time.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A dialysis system, comprising:
an extracorporeal blood container;
one or more light emitters configured to generate light at a plurality of wavelengths;
one or more sensors configured to detect the light originating from the one or more light emitters after the light has traversed the extracorporeal blood container, wherein the one or more sensors are in communication with a processor; and
the processor, wherein the processor is configured to:
receive, from the one or more sensors, a first plurality of measurements corresponding to the plurality of wavelengths, wherein the first plurality of measurements are indicative of respective amounts of absorption associated with contents of the extracorporeal blood container at a first time for the plurality of wavelengths;
receive, from the one or more sensors, a second plurality of measurements corresponding to the plurality of wavelengths, wherein the second plurality of measurements are indicative of respective amounts of absorption associated with contents of the extracorporeal blood container at a second time for the plurality of wavelengths;
determine, based on the first plurality of measurements and the second plurality of measurements, that an air bubble is present in the extracorporeal blood container; and
execute an action in response to determining that the air bubble is present in the extracorporeal blood container.

2. The dialysis system of claim 1, wherein the processor is further configured to:
monitor the one or more sensors based on a pre-defined sampling rate, and
wherein the processor is configured to receive the first plurality of measurements and receive the second plurality of measurements based on monitoring the one or more sensors.

3. The dialysis system of claim 2, wherein the processor is configured to monitor the one or more sensors by:
determining, based on the pre-defined sampling rate, the first time and the second time;
providing one or more first instructions to the one or more sensors to sample sensor measurements at the first time, wherein receiving the first plurality of measurements is in response to providing the one or more first instructions; and
providing one or more second instructions to the one or more sensors to sample sensor measurements at the second time, wherein receiving the second plurality of measurements is in response to providing the one or more second instructions.

4. The dialysis system of claim 1, wherein the plurality of wavelengths comprise a first wavelength and a second wavelength,
wherein the first plurality of measurements comprise a first measurement associated with the first wavelength and a second measurement associated with the second wavelength,
wherein the second plurality of measurements comprise a third measurement associated with the first wavelength and a fourth measurement associated with the second wavelength, and
wherein the processor is configured to determine the air bubble is present in the extracorporeal blood container based on the first measurement, the second measurement, the third measurement, and the fourth measurement.

5. The dialysis system of claim 4, wherein the processor is configured to determine that the air bubble is present in the extracorporeal blood container by:
determining one or more first values associated with the first time based on the first measurement and the second measurement;
determining one or more second values associated with the second time based on the third measurement and the fourth measurement; and
determining that the air bubble is present in the extracorporeal blood container based on the one or more first values and the one or more second values.

6. The dialysis system of claim 5, wherein the one or more first values comprise a first light absorption value associated with the first wavelength and a second light absorption value associated with the second wavelength, and wherein the one or more second values comprise a third light absorption value associated with the first wavelength and a fourth light absorption value associated with the second wavelength.

7. The dialysis system of claim 5, wherein the one or more first values comprise a first ratio associated with the first measurement and the second measurement, and wherein the one or more second values comprise a second ratio associated with the third measurement and the fourth measurement.

8. The dialysis system of claim 4, wherein the plurality of wavelengths further comprise a third wavelength,
wherein the first plurality of measurements further comprise a fifth measurement associated with the third wavelength,
wherein the second plurality of measurements further comprise a sixth measurement associated with the third wavelength, and
wherein the processor is configured to determine that the air bubble is present in the extracorporeal blood container based on the first measurement, the second measurement, the third measurement, the fourth measurement, the fifth measurement, and the sixth measurement.

9. The dialysis system of claim 8, wherein the processor is configured to determine that the air bubble is present in the extracorporeal blood container by:
determining one or more first values associated with the first time based on the first measurement, the second measurement, and the fifth measurement;
determining one or more second values associated with the second time based on the third measurement, the fourth measurement, and the sixth measurement; and
determining that the air bubble is present in the extracorporeal blood container based on the one or more first values and the one or more second values.

10. The dialysis system of claim 1, wherein the extracorporeal blood container comprises at least one of: an extracorporeal blood chamber or an extracorporeal tubing.

11. A method, comprising:
receiving, from one or more sensors, a first plurality of measurements corresponding to a plurality of wavelengths, wherein the first plurality of measurements are indicative of respective amounts of absorption associated with contents of an extracorporeal blood container at a first time for the plurality of wavelengths, wherein the one or more sensors are configured to detect light originating from one or more light emitters after the light has traversed the extracorporeal blood container;

receiving, from the one or more sensors, a second plurality of measurements corresponding to the plurality of wavelengths, wherein the second plurality of measurements are indicative of respective amounts of absorption associated with contents of the extracorporeal blood container at a second time for the plurality of wavelengths;

determining, based on the first plurality of measurements and the second plurality of measurements, that an air bubble is present in the extracorporeal blood container; and executing an action in response to determining that the air bubble is present in the extracorporeal blood container.

12. The method of claim 11, further comprising:
monitoring the one or more sensors based on a pre-defined sampling rate, and
wherein receiving the first plurality of measurements and receiving the second plurality of measurements are based on monitoring the one or more sensors.

13. The method of claim 12, wherein monitoring the one or more sensors comprises:
determining, based on the pre-defined sampling rate, the first time and the second time;
providing one or more first instructions to the one or more sensors to sample sensor measurements at the first time, wherein receiving the first plurality of measurements is in response to providing the one or more first instructions; and
providing one or more second instructions to the one or more sensors to sample sensor measurements at the second time, wherein receiving the second plurality of measurements is in response to providing the one or more second instructions.

14. The method of claim 11, wherein the plurality of wavelengths comprise a first wavelength and a second wavelength,
wherein the first plurality of measurements comprise a first measurement associated with the first wavelength and a second measurement associated with the second wavelength,
wherein the second plurality of measurements comprise a third measurement associated with the first wavelength and a fourth measurement associated with the second wavelength, and
wherein determining the air bubble is present in the extracorporeal blood container is based on the first measurement, the second measurement, the third measurement, and the fourth measurement.

15. The method of claim 14, wherein determining that the air bubble is present in the extracorporeal blood container comprises:
determining one or more first values associated with the first time based on the first measurement and the second measurement;
determining one or more second values associated with the second time based on the third measurement and the fourth measurement; and
determining that the air bubble is present in the extracorporeal blood container based on the one or more first values and the one or more second values.

16. The method of claim 15, wherein the one or more first values comprise a first light absorption value associated with the first wavelength and a second light absorption value associated with the second wavelength, and wherein the one or more second values comprise a third light absorption value associated with the first wavelength and a fourth light absorption value associated with the second wavelength.

17. The method of claim 15, wherein the one or more first values comprise a first ratio associated with the first measurement and the second measurement, and wherein the one or more second values comprise a second ratio associated with the third measurement and the fourth measurement.

18. The method of claim 14, wherein the plurality of wavelengths further comprise a third wavelength,
wherein the first plurality of measurements further comprise a fifth measurement associated with the third wavelength,
wherein the second plurality of measurements further comprise a sixth measurement associated with the third wavelength, and
wherein determining that the air bubble is present in the extracorporeal blood container is based on the first measurement, the second measurement, the third measurement, the fourth measurement, the fifth measurement, and the sixth measurement.

19. The method of claim 18, wherein determining that the air bubble is present in the extracorporeal blood container comprises:
determining one or more first values associated with the first time based on the first measurement, the second measurement, and the fifth measurement;
determining one or more second values associated with the second time based on the third measurement, the fourth measurement, and the sixth measurement; and
determining that the air bubble is present in the extracorporeal blood container based on the one or more first values and the one or more second values.

20. A non-transitory computer-readable storage medium having processor-executable instructions stored thereon, wherein the processor-executable instructions, when executed by a processor, facilitate:
receiving, from one or more sensors, a first plurality of measurements corresponding to a plurality of wavelengths, wherein the first plurality of measurements are indicative of respective amounts of absorption associated with contents of an extracorporeal blood container at a first time for the plurality of wavelengths, wherein the one or more sensors are configured to detect light originating from one or more light emitters after the light has traversed the extracorporeal blood container;
receiving, from the one or more sensors, a second plurality of measurements corresponding to the plurality of wavelengths, wherein the second plurality of measurements are indicative of respective amounts of absorption associated with contents of the extracorporeal blood container at a second time for the plurality of wavelengths;
determining, based on the first plurality of measurements and the second plurality of measurements, that an air bubble is present in the extracorporeal blood container; and
executing an action in response to determining that the air bubble is present in the extracorporeal blood container.

21. The dialysis system of claim 1, wherein the processor is configured to execute the action by generating an alarm in response to determining that the air bubble is present in the extracorporeal blood container.

22. The dialysis system of claim 1, further comprising:
a pump, and
wherein the processor is configured to execute the action by stopping a pumping operation of the pump in response to determining that the air bubble is present in the extracorporeal blood container.

\* \* \* \* \*